United States Patent
Nguyen et al.

(10) Patent No.: US 10,663,412 B2
(45) Date of Patent: May 26, 2020

(54) DEVICE FOR ANALYZING A FLUID IN A SAMPLE OF POROUS MEDIUM, AND CORRESPONDING METHOD

(71) Applicant: TOTAL SA, Courbevoie (FR)

(72) Inventors: Michel Nguyen, Bourdettes (FR); Gilles Puyou, Arbus (FR)

(73) Assignee: TOTAL SA, Courbevoie (FR)

( * ) Notice: Subject to any disclaimer, the term of this patent is extended or adjusted under 35 U.S.C. 154(b) by 216 days.

(21) Appl. No.: 15/532,780

(22) PCT Filed: Dec. 3, 2014

(86) PCT No.: PCT/IB2014/002915
§ 371 (c)(1),
(2) Date: Jun. 2, 2017

(87) PCT Pub. No.: WO2016/087890
PCT Pub. Date: Jun. 9, 2016

(65) Prior Publication Data
US 2017/0370858 A1    Dec. 28, 2017

(51) Int. Cl.
*G01N 15/08* (2006.01)
*G01N 23/04* (2018.01)
*G01N 33/28* (2006.01)

(52) U.S. Cl.
CPC ........... *G01N 23/04* (2013.01); *G01N 15/088* (2013.01); *G01N 33/28* (2013.01)

(58) Field of Classification Search
CPC ...... G01N 23/04; G01N 23/02; G01N 23/083; G01N 23/12; G01N 23/06;
(Continued)

(56) References Cited

U.S. PATENT DOCUMENTS 5,269,469 A * 12/1993 Graenicher ............ G01N 15/02
241/159
2007/0274443 A1   11/2007 Groves et al.
(Continued)

FOREIGN PATENT DOCUMENTS

JP      2006275664 A    10/2006
JP      2007101259 A     4/2007
(Continued)

OTHER PUBLICATIONS

Lisa Cavé et al., "A technique for estimating one-dimensional diffusion coefficients in low-permeability sedimentary rock using X-ray radiography: Comparison with through-diffusion measurements", Journal of Contaminant Hydrology 103, 2009, pp. 1-12, journal homepage: www.elseviar.com/locate/jconhyd.
Angela Cantatore and Pavel Müller; Introduction to computed tomography; Manufacturing Engineering, Department of Mechanical Engineering, Technical University of Denmark, Mar. 2011; pp. 1-78, XP055516940.
(Continued)

*Primary Examiner* — Jurie Yun
(74) *Attorney, Agent, or Firm* — Pearne & Gordon LLP (57) ABSTRACT

The device comprises: a measurement cell, configured for receiving a sample of porous medium containing a fluid comprising one or more phases; a X-ray source, configured for illuminating the measurement cell with X-rays; a detector, placed opposite the X-ray source with regards to the measurement cell, the detector being configured for receiving X-rays arising from the sample contained in the measurement cell. The X-ray source is configured for illuminating simultaneously at least a surface of the sample without relative movement between the X-ray source and the sample, the detector comprising a plurality of sensing areas configured for selectively detecting X-rays arising from different points on the surface of the sample.

16 Claims, 3 Drawing Sheets

(58) Field of Classification Search
CPC ....... G01N 23/20008; G01N 23/20033; G01N 33/28; G01N 15/08; G01N 15/088; G01N 15/00; G01N 15/082; G01N 15/0826; G21K 5/08
USPC .................................. 378/52, 62, 66, 68, 208
See application file for complete search history.

(56) References Cited

U.S. PATENT DOCUMENTS

| | | | |
|---|---|---|---|
| 2009/0141865 A1* | 6/2009 | Delaney | G01N 23/2204 378/160 |
| 2011/0013748 A1 | 1/2011 | Ichizawa et al. | |
| 2013/0129041 A1 | 5/2013 | Runft | |
| 2014/0133623 A1* | 5/2014 | Creux | G01N 23/046 378/19 |
| 2014/0270071 A1* | 9/2014 | Shirota | G01N 23/04 378/62 |

FOREIGN PATENT DOCUMENTS

| | | |
|---|---|---|
| JP | 2011022030 A | 2/2011 |
| JP | 2013532823 A | 8/2013 |
| WO | 2005/084351 A2 | 9/2005 |
| WO | 2012/164090 A1 | 12/2012 |

OTHER PUBLICATIONS

International Search Report for PCT/IB2014/002915 dated Mar. 31, 2015.
Ott, H. et al. Core-flood experiment for transport of reactive fluids in rocks: IN: Review of Scientific Instruments, American Institute of Physics 2012, pp. 084501-1-084501-16.
Wildenschild, Dorthe et al. "X-ray imaging and analysis techniques for quantifying pore-scale structure and processes in subsurface porous medium systems" IN: Advances in Water Resources 2013, pp. 217-246.
Winthers, "X-ray nanotomography", Materials Today, vol. 10, No. 12, Dec., 2007, pp. 1-9.

* cited by examiner

DEVICE FOR ANALYZING A FLUID IN A SAMPLE OF POROUS MEDIUM, AND CORRESPONDING METHOD

This is a National Stage application of PCT international application PCT/IB2014/002915, filed on Dec. 3, 2014 which is incorporated herein by reference in it's entirety.

The present invention relates to a device for analyzing a fluid in a sample of porous medium, comprising:
- a measurement cell, configured for receiving a sample of porous medium containing a fluid comprising one or more phases;
- a X-ray source, configured for illuminating the measurement cell with X-rays;
- a detector, placed opposite the X-ray source with regards to the measurement cell, the detector being configured for receiving X-rays arising from the sample contained in the measurement cell.

The device is intended in particular for studying a multiphase fluid flow in an opaque porous medium such as a core of rock, by using X-rays.

Such a device advantageously collects data to calculate local properties of the fluid in the porous medium at different positions in the porous medium, in particular for discriminating among the different phases of the fluid permeating the medium at the different positions and for obtaining local proportions or saturations of the different phases.

Such an analysis is generally carried out in a rock sample, to simulate fluid permeation and/or migration in a fluid bearing formation located underground.

In known devices, a sample of a porous medium containing fluid is inserted in a cell on a moving bench. An X-ray source is placed on one side of the sample and a punctual detector is positioned on the other side of the sample. X-rays are emitted by the source, go through the sample at a punctual position on the sample, and are recovered by the detector. The detector detects a photon count. Depending on the absorbance of the sample, the fluid content at the measurement point can be determined, for example using Beer-Lambert law.

In order to get information at different positions of the sample, successive punctual measurements are carried out along the axis of the sample, by moving the sample or the source and detector relatively to each other (the source using the moving bench).

Such a method is tedious to operate. It has a long acquisition time. The visualization of the sample can be carried out only along a line along the central axis of the sample with a punctual determination at each point along the line.

The information collected at different points along the line is not simultaneous, because the measurements at each point must be made sequentially along the line with a separate acquisition for each point.

It is therefore very difficult to obtain dynamic measurements, in case the fluid located in the porous sample flows in the sample.

Moreover, the measurement of fluid properties is complex to make. Indeed, the porous medium containing the fluid is very opaque and the fluids have an attenuating power much lower than the solid matrix receiving the fluid. Moreover, the effect of the difference in fluid content on the signal collected at the detector is very low and almost negligible in comparison with the effect of the solid matrix containing the fluid on the signal.

One aim of the invention is to obtain a device which is able to analyze precisely and dynamically the local properties of a fluid contained in a porous opaque medium, with a fast acquisition time.

To this aim, the subject-matter of the invention is a device of the preceding type, characterized in that the X-ray source is configured for illuminating simultaneously at least a surface of the sample without relative movement between the X-ray source and the sample, the detector comprising a plurality of sensing areas configured for selectively detecting X-rays arising from different points on the surface of the sample.

The device according to the invention may comprise one or more of the following features, taken solely, or according to any technical possible combination:
- it comprises a reference sample, positioned to be illuminated simultaneously with the measurement cell by the X-ray source, without relative movement between the X-ray source and the sample, the detector having at least one sensing area able to detect X-rays arising from the reference sample.
- the detector comprises a two-dimensional array of selective sensing areas configured for selectively detecting X-rays arising from different points on the surface of the sample.
- the detector has a sensing area at least as wide as the projection of the sample contained in the measurement cell on the detector;
- the X-ray source is configured for illuminating the whole sample contained in the measurement cell, the detector comprising sensing areas able to detect X-rays arising from different points spread on the surface of the sample and outside of the sample.
- the X-ray source comprises an hyperstable X-ray generator.
- the X-ray source is intended to be permanently activated, the device comprising a shutter, positioned between the X-ray source and the measurement cell, the shutter being mobile between a position preventing the illumination of the measurement cell by the X-ray source and a position illuminating the measurement cell.
- it comprises a unit for controlling temperature and pressure in the measurement cell.
- it comprises an analyzing unit able to determine a local property of the fluid at a plurality of positions of the sample, based on signals detected simultaneously by sensing areas at the given measurement time without relative movement between the X-ray source and the sample.
- it comprises at least a shielding assembly placed laterally around the measurement cell.
- the measurement cell comprises a hollow container, receiving the sample of porous medium containing fluid, at least one plug closing the hollow container, the at least one plug advantageously comprising an internal open volume intended to receive fluid arising from the sample or directed towards the sample, the X-ray source being configured for illuminating the open volume, the detector comprising at least a selective sensing area able to receive X-ray arising from the open volume.

The invention also relates to a method of analyzing a fluid comprising one or more phases in a sample of porous medium, comprising the following steps:
- providing a device as indicated above, the measurement cell containing a sample of porous medium containing fluid;

illuminating at least a surface of the sample with the X-ray source, without relative movement between the X-ray source and the sample;

selectively detecting X-rays arising from different points of the surface by a plurality of sensing areas of the detector;

determining a local property of the fluid at a plurality of positions of the sample, based on signals detected simultaneously by sensing areas.

The method according to the invention may comprise one or more of the following features, taken solely, or according to any technical possible combination:

the illumination step comprises passing X-rays arising from the X-ray source through a reference sample simultaneously with illuminating the measurement cell and selectively detecting X-rays arising from the reference sample with a selective sensing area of the detector.

controlling the pressure of the sample in the measurement cell, advantageously above the atmospheric pressure, and controlling the temperature of the sample in the measurement cell, during the illumination step.

the determination step comprises calculating a fluid content in one or more phase at least at a plurality of positions on the surface of the sample, based on the signal detected by each sensing area.

repeating the steps of illuminating at least a surface of the sample with the X-ray source, of selectively detecting X-rays arising from different points of the surface by a plurality of sensing areas of the detector and of determining a local property of the fluid at a plurality of positions of the sample, based on signals detected simultaneously by sensing areas, at several measurement times, without relative movement between the X-ray source and the sample, advantageously at a frequency below 1 Hz.

The invention will be better understood, upon reading of the following description, given purely as a non-limiting example, and made in reference to the appended drawings, in which.

Figure 1:
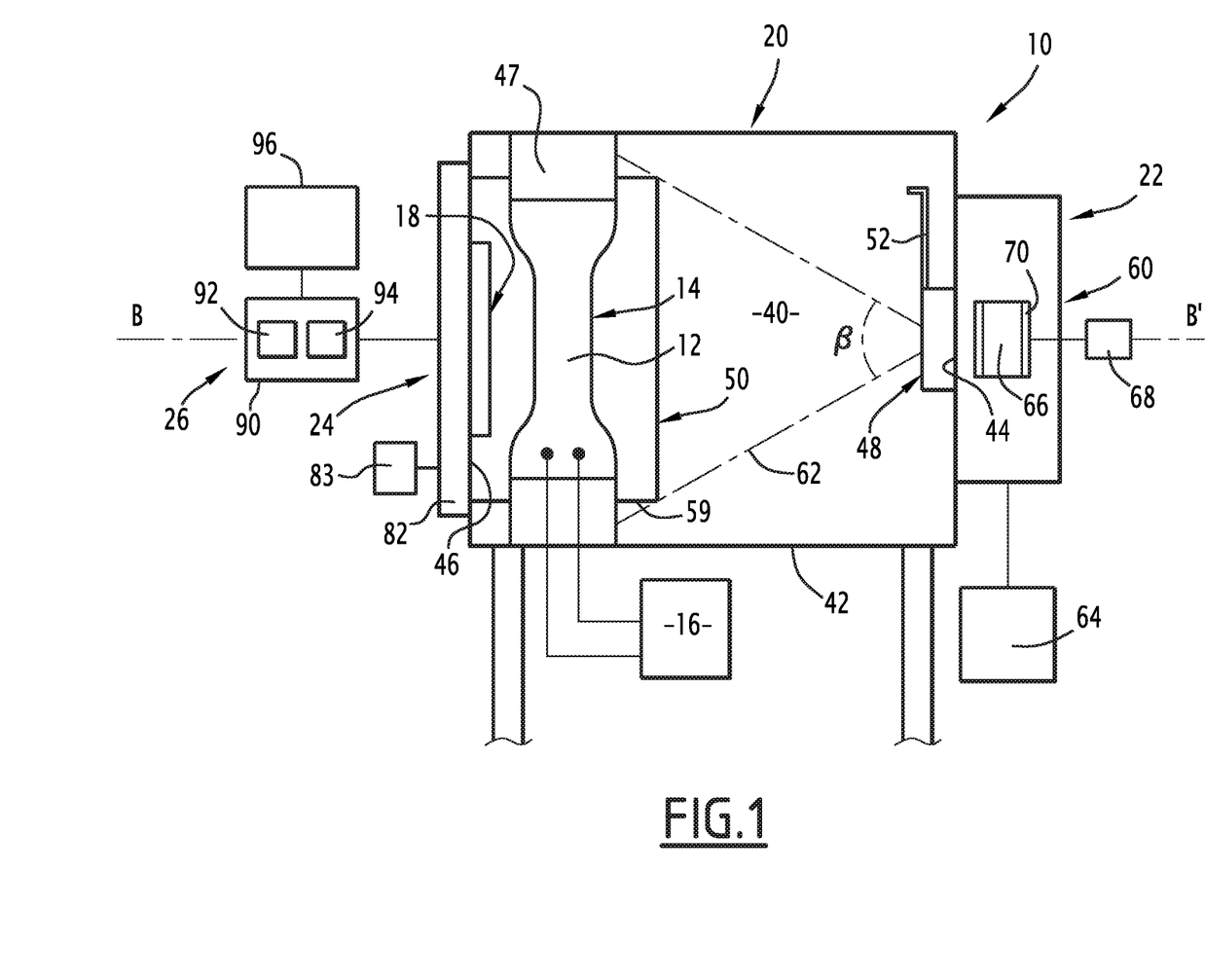
FIG. 1 is a schematic front view, partially in cross section, of a first analyzing device according to the invention.

A first analysis device 10 according to the invention is illustrated in FIG. 1. The device is for analyzing a fluid behavior in a porous medium, such as in a rock or sediment sample comprising pores.

Figure 3:
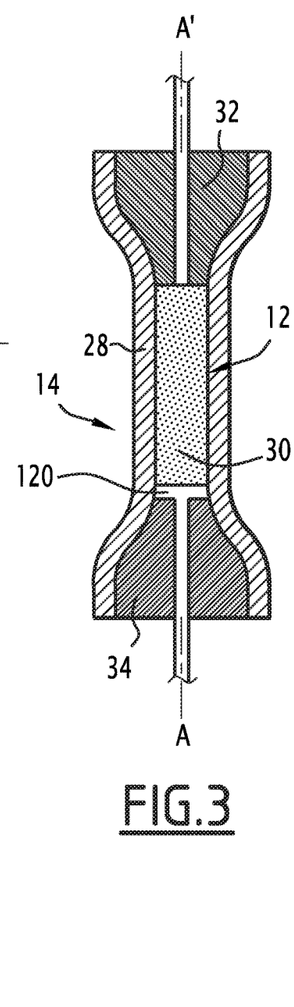
FIG. 3 is view, taken in cross section along a median axis, of a first measurement cell of the device of FIG. 1.

The sample 12 is shown in FIG. 3. It has a porosity generally comprised between 0% and 99%.

The sample 12 has for example a height of more than 1 cm and comprised between 10 cm and 50 cm in a particular embodiment.

The device 10 allows for example the determination of a local property of the fluid at various positions in a projection of the sample 12 in a plane.

The determination can be carried out for example during permeation of the fluid into the pores of the porous sample 12.

The fluid is for example a multiphase fluid, such as a hydrocarbonaceous fluid comprising a gas phase and a liquid phase. The liquid phase advantageously comprises a water phase and an oil phase.

In one typical analysis, the fluid is injected at a first point in the sample 12, for example at one end of the sample 12. The evolution of fluid permeation along the sample 12 is assessed by the device 10 according to the invention, by measuring local properties of the fluid, such as proportions in the different phases, at different positions at several measurement times.

The permeation of the fluid is monitored in specific pressure and temperature conditions which are controlled in the device 10 according to the invention. These temperature and pressure conditions generally correspond to the temperature and pressure in a subterranean formation containing oil and gas.

In reference to FIG. 1, the device 10 comprises a measurement cell 14 containing the porous sample 12, and a unit 16 for controlling temperature and/or pressure into the measurement cell 14.

The device 10 further comprises a reference sample 18 and an enclosure 20 intended to contain the measurement cell 14 and the reference sample 18.

The device 10 also comprises an X-ray hyperstable source 22, placed on one side of the enclosure 20 and a detector 24 located on an opposite side of the enclosure 20, at the opposite side of the X-ray source 22 with regard to the measurement cell 14.

The device 10 further comprises an analyzing unit 26 able to receive the measurements made by the detector 24 and to determine at least a local property of the fluid in the sample.

The measurement cell 14 is shown in FIG. 3. It comprises a hollow container 28 defining a sample receiving cavity 30. It also comprises at least one plug 32, 34 to close the sample receiving cavity 30.

In the example of FIG. 3, the hollow container 28 is tubular. It is for example made of a material more transparent to X-ray than the sample 12 it contains. The material is for example carbon. Here, the sample 12 is cylindrical. In a variant, the sample 12 is a parallelepiped.

In FIG. 3, the measurement cell 14 comprises a central tubular part containing the sample 12 and two end parts, wider than the central part, receiving the plugs 32, 34.

The plugs 32, 34 seal the cavity 30 in an impervious manner.

The unit 16 is able to control the temperature and the pressure of the sample 12 in the cavity 30. It is for example able to maintain the atmospheric pressure or to apply a pressure higher than the atmospheric pressure, for example of more than 50 bars, in particular of more than 100 bars and for example comprised between 0 bars and 800 bars, for example between 200 bars and 650 bars.

It is also able to maintain a temperature in the cavity of more than 50° C., in particular of more than 100° C. and comprised between 100° C. and 160° C.

The measurement cell 14 is able to be introduced in the enclosure 20 and to be maintained in position in the enclosure 20, for example with its axis A-A' positioned vertically. In a variant, the axis A-A' is positioned horizontally or according to another orientation.

The measurement cell 14 is interposed between the X-ray source 22 on the one side and the detector 24 on the other side, defining together an axis B-B' of illumination.

The reference sample 18 comprises a gauge block made of a dry mineral material, such as rock. The rock is for example chosen from sandstone, or carbonate, or any reservoir rock or source rock. The X-ray attenuation of the gauge block is close to the attenuation observed with the sample 12 contained in the measurement cell 14.

The composition of the gauge block is preferably similar to the composition of the sample 12.

The reference sample 18 is placed in the enclosure 20, between the X-ray source 22 and the detector 24, to be illuminated simultaneously with the measurement cell 14. It is positioned away from the measurement cell 14 and from the illumination axis B-B', so as to provide an image on the detector 24 which is distinct from the image of the measurement cell 14 and of the sample 12.

The enclosure 20 defines a confinement volume 40 for confining the X-rays produced by the X-ray source 22, and for receiving the sample measurement cell 14 and the reference sample 18. It comprises absorbent walls 42 for example made of lead.

The volume of the enclosure 20 is generally comprised between 0.5 m$^3$ and 2 m$^3$. The walls 42 of the enclosure define at least one upstream axial opening 44 facing the source 22 in order to allow the introduction of X-rays produced by the X-ray source 22 in the confinement volume 40 and at least a downstream axial opening 46 placed facing the detector 24 and facing the upstream opening 44, to allow the illumination of the detector 24 with the X-rays arising from the confinement volume 40, in particular the X-rays arising from the measurement cell 14 and from the reference sample 18.

In the embodiment shown in FIG. 1, the enclosure 20 further comprises a holder 47 for maintaining in position the measurement cell 14, a shutter assembly 48 for controlling the entry of X-rays into the confinement volume 40 and a shielding assembly 50, for protecting the measurement cell 14 from reflective X-rays.

The shutter 48 comprises a shutting plate 52 mobile between a position preventing X-rays emitted by the X-ray source 22 to enter the confinement volume 40 and a position allowing passage of X-rays emitted by the X-ray source 22 into the confinement volume 40.

Hence, the X-ray source 22 can remain permanently active. The shutting plate 52 is moved in its preventing position when an access to the confinement volume 40 is needed. The measurement cell 14 can then be introduced into the holder 47, without having to shut down the X-source 22, which maintains the stability of the X-ray source 22.

The shielding assembly 50 for example comprises at least a partition 59 located laterally with regard to the measurement cell 14 in order to shield the measurement cell 14 from reflective X-rays arising from the walls 42 of the volume 40 or/and from other parts of the volume 40.

Figure 2:
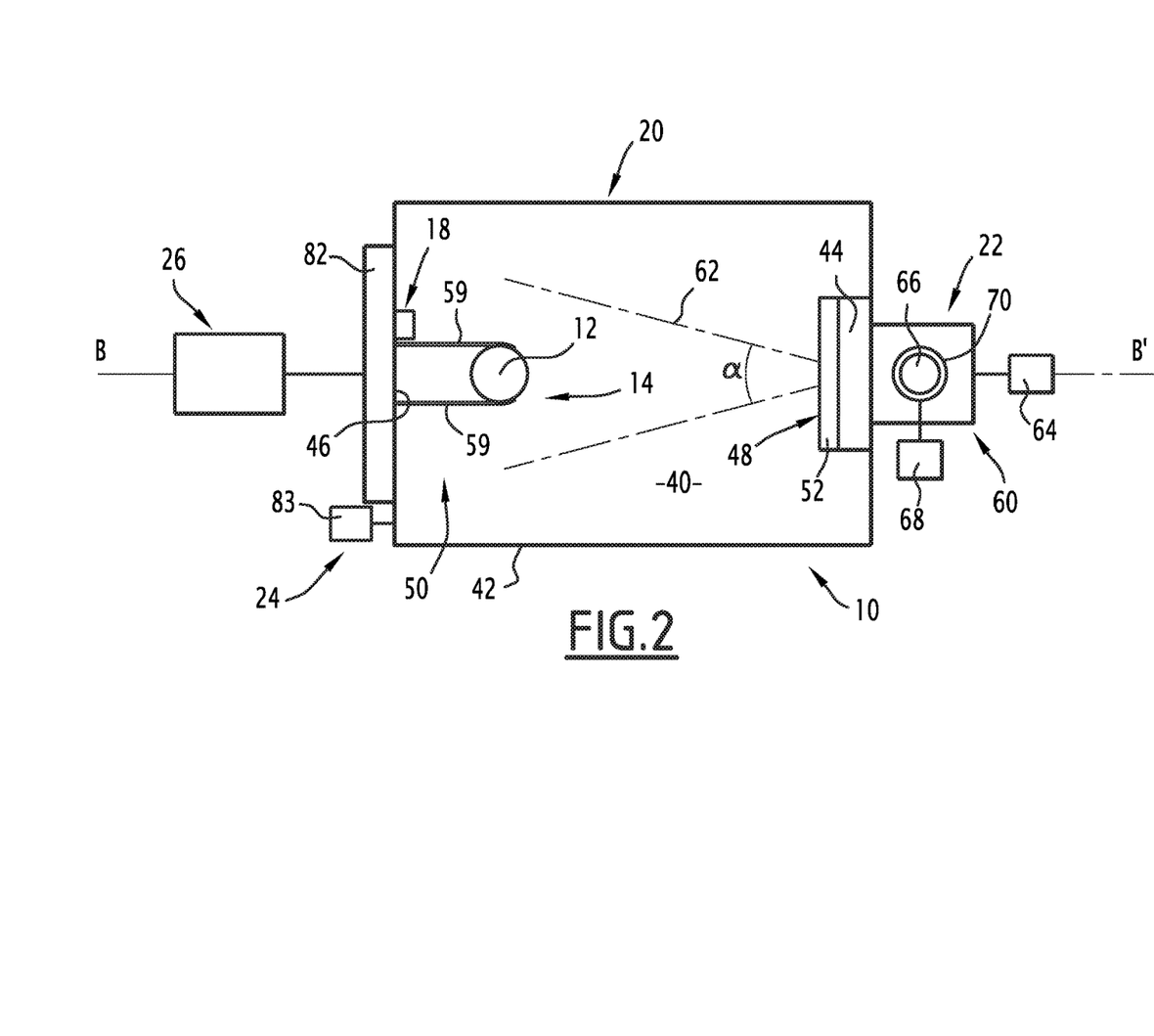
FIG. 2 is an upper view from the device of FIG. 1, taken partially in cross section.

In the example of FIG. 2, the shielding assembly 50 comprises two lateral parallel partitions 59 surrounding laterally the measurement cell 14 parallel to the illumination axis B-B'.

According to the invention, the X-ray source 22 comprises a hyperstable X-ray generator 60 able to produce a very stable beam 62 of X-rays to illuminate the sample 12 contained into the measurement cell 14 and the reference cell 18. It further comprises a tension and current controller 64 to supply electrical power to the generator 60.

The beam 62 is able to illuminate at least a surface of the sample 12 and preferably the whole porous sample 12, without relative movement between the X-ray source 22 and the porous sample 12.

The term "at least a surface of the sample" means that the illumination is not punctual. The surface of the sample 12 illuminated by the beam is generally greater than 0.01 cm$^2$. Advantageously, the beam 62 is able to totally illuminate the sample 12.

The horizontal aperture angle α and the vertical aperture angle ß of the beam 62 are set so that the whole zone of interest including the sample 12 and the reference sample 18 is irradiated simultaneously. These angles α, ß are limited to that zone to reduce at maximum scattering radiations.

The term "hyperstable" generally means that the number of X-photons produced by the generator in a given solid angle is substantially constant along time. The variation of the average number of photons per second produced by the impulsions of the generator 60 is for example equal to a nominal value plus or minus 0.5% along time. The dose can be measured with an ionizing chamber in taking into account the environmental corrections.

A hyperstable generator 60 is stable with a nominal power but the voltage must be limited to 80% of the nominal voltage to avoid dark current emission which generate the unstability of the dose.

For example, when the nominal power of emission is equal to 100 kV, the hyperstable generator produces a stable number of photons per impulsion at a power of emission up to 80 kV.

The power of emission is defined here by the high voltage applied to the generator 60. This high voltage is for example comprised between 60 kV and 160 kV, in particular between 80 kV and 120 kV.

In the example of FIG. 1, the hyperstable generator 60 comprises a ceramic tube 66 and a temperature controller 68 able to control the temperature of the ceramic tube 66.

The ceramic tube 66 comprises a tungsten filament and is constantly heated so that the electron flux is constant and stable. The tube 66 is designed so that no grid effect can influence the beam from electrons trapped on the insulator.

The temperature controller 68 comprises for example a cooling fluid able to circulate in a double wall 70 located around the ceramic tube 66. The temperature of the tube 66 is for example maintained at a target temperature between 25° C. and 35° C.

The hyperstable X-ray generator 60 is for example a generator marketed under the reference GXC-130 by X-Ris.

The tension and current controller 64 is able to produce a stabilized current and tension to supply the hyperstable generator 60. Advantageously, during more than 1 hour, in particular during several hours, the variation of tension is smaller than 0.1% (in kV) and the variation in intensity is smaller than 1% (in mA).

The detector 24 comprises at least one line of sensing areas 80 able to selectively detect X-rays arising from the source 22 potentially having passed through the surface of the sample 12 and through the reference sample 18.

Figures 4, 5:
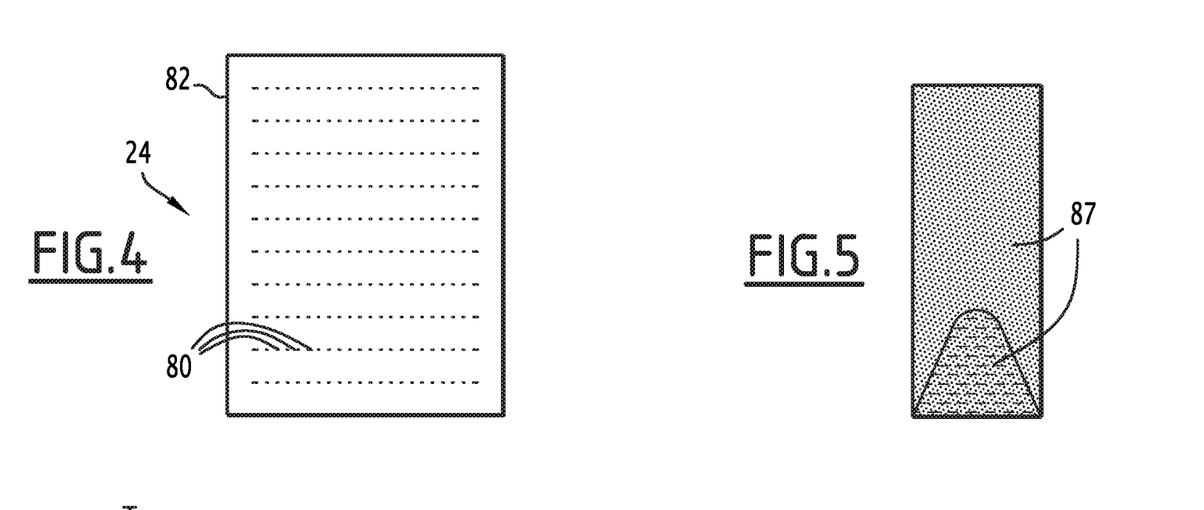
FIG. 4 is an elevation view of the detector of the device of FIG. 1.
FIG. 5 is a representation of a map of fluid proportions in a sample introduced in the measurement cell of FIG. 3, at a given measurement time.

In the example of FIG. 4, the detector 24 comprises a flat panel 82 carrying an array of sensing areas 80 defining pixels in the flat panel 82. The flat panel 82 is for example a planar amorphous silicon flat panel, marketed under the name DEREO WA. The detector advantageously comprises a temperature control unit 83 controlling the temperature of the flat panel 82.

Each pixel formed by a sensing area 80 is able to selectively receive a number of X-photons arising from the source 22, corresponding selectively to a particular position in a projection of the sample 12 in a vertical plane perpendicular to the illumination axis B-B', or to a particular position in the reference sample 18, or to a position outside of the samples 12, 18.

At any measurement time, each sensing area 80 is able to sense the number of X-photons received during a sampling interval for example smaller than 15 s, generally around 10 s and potentially comprised between 0.5 s and 10 s.

The number of X-photons received by each sensing area 80 is representative of the absorbance of the signal at the position detected by the sensing area 80.

Figure 7:
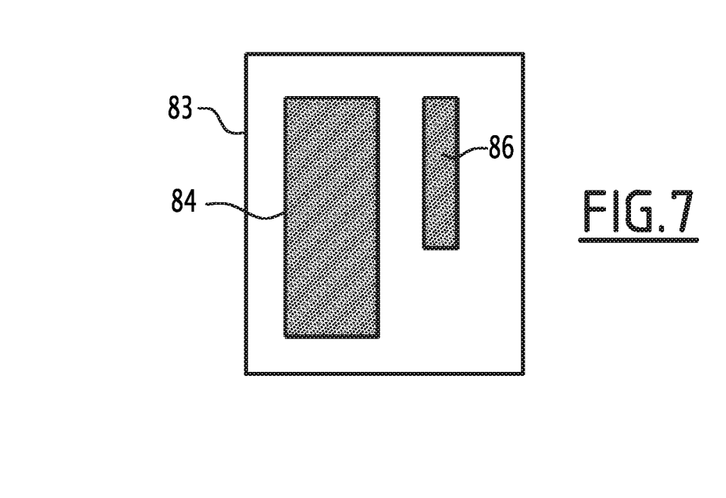
FIG. 7 is a view of a radiographic image measured by the detector of FIG. 4.

The number of X-photons provides a level of grey in a radiographic image 83 of the beam 62 after its passage through the sample 12, or through the reference sample 18 or through the confinement volume 40 away from the sample 12 and from the reference sample 18, as shown in FIG. 7.

The image 83 representing the level of gray at different positions on the sample 12 (region 84 in FIG. 7) and on the reference sample 18 (region 86 in FIG. 7) at a given measurement time can be obtained by the detector 24, based on the signals produced by each sensing area 80 of the detector 24.

In the region 84, each pixel is representative of the absorbance of the X-ray beam having passed through the sample 12 at the corresponding position in a projection of the sample 12 in a vertical plane.

The analyzing unit 26 comprises a calculator 90 having a processor 92 and a memory 94, and a man/machine interface 96.

The memory 94 contains software applications which can be executed in the processor 92. Among the software applications, the memory 94 contains at least one software module able to receive, at each measurement time, a signal representative of the number of photons measured by each sensing area 80.

The memory 94 further contains a software module able to calculate at least a property of the fluid contained in the porous medium, for example a proportion in each phase. The calculation is based on the signal produced by the sensing area 80. It is also based on at least one reference image, and preferentially based on two reference images in which a correlation is made between the property and the signal at each position. It is also advantageously based on a signal produced by a sensing area 80 receiving X-rays arising from the reference sample 18.

The memory 94 also contains a software module able to display on the man/machine interface 96 a representation shown in FIG. 5 of the fluid property (here the level of proportion) at each position of the sample 12 corresponding to a sensing area 80, at a given measurement time. The software module is also able to display a curve shown in FIG. 6 of the evolution of the fluid property along time at a particular position in the sample 12.

In the example of FIG. 5, the local proportions 87 of the phases in the fluid at the different positions are displayed with a color scale, showing the impregnation of the fluid.

Figure 6:
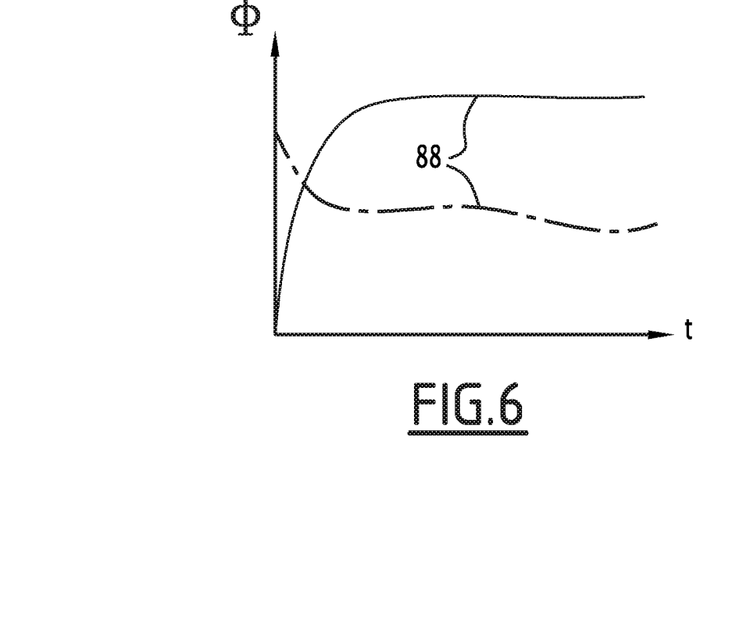
FIG. 6 is a graph representing the concentration in each phase at a particular position in the sample of FIG. 3, as a function of time.

In FIG. 6, the evolutions of the proportions 88 in gas phase, and in liquid phase are represented versus time at a position of the sample 12 corresponding to a sensing area 80.

A method for measuring and analyzing a fluid in a sample of porous medium 12 according to the invention will be now described.

The method is carried out in the device 10 previously described, in view of FIGS. 1 to 4.

Initially, the source 22 is supplied with a stabilized current and tension arising from the tension and current controller 64. The hyperstable generator 60 is permanently powered and stabilized to produce a stable beam of X-rays 62.

The sample 12 is then inserted into the measurement cell 14. The measurement cell 14 is closed by the plugs 32, 34 and is sealed.

The shutter plate 52 is then passed in its position for preventing the beam 62 to enter the confinement volume 40. The enclosure 20 is opened to access the volume 40.

The measurement cell 14 is put in place in the holder 47. In the example of FIG. 1, the measurement cell 14 is positioned with its axis A-A' vertical. The axis of the reference sample 18 is also vertical.

The measurement cell 14 is then connected to the unit 16 for controlling temperature and pressure to set a measurement target temperature and a measurement target pressure in the measurement cell 14.

The measurement target temperature is for example set between 20° C. and 160° C. and the measurement target pressure is set between 1 bar and 800 bars.

Once the temperature and pressure of the sample 12 are stable, the shutter plate 52 is placed in its position for illuminating the confinement volume 40 with the X-ray beam 62.

A first measurement in the absence of fluid is then carried out to obtain a reference image of the sample 12 providing reference signals at each position of the sample 12 corresponding to a sensing area 80.

Then, fluid is progressively injected into the sample 12. A series of measurements at different measurement times is then carried out.

These measurements are for example carried out at a frequency of about 0.1 Hz and generally below 1 Hz.

At each measurement time, the beam 62 illuminates the sample 12 contained in the measurement cell 14, the reference sample 18 and the volume surrounding these samples 12, 18. The detector 24 is activated to measure, at each sensing area 80, a signal representative of the number of counts of X photons having been transmitted through the porous sample 12, the reference sample 18 and the surrounding area.

An image 83, shown in FIG. 7 is created with a region 84 of pixels corresponding to the sample 12, and a region 86 of pixels corresponding to the reference sample.

Each pixel on the region 84 corresponds to a particular position in the sample 12. All the positions which have been illuminated of the sample 12 are measured simultaneously, which allows building a map of fluid properties in the sample at the measurement time.

Then, the analyzing unit 26 gathers the signals obtained at each sensing area 80 of detector 24 at the measurement time, deletes the contribution resulting from the porous medium, based on the reference measurements and based on the measurement in the reference sample 18, and extracts at least an information representative of a fluid property at each position in the sample 12.

Based on a model, the analyzing unit 26 then calculates the fluid property at each position, for example the proportions in at least the gas phase and the liquid phase at each position.

The same steps are repeated at each measurement time, in order to determine the evolution of the fluid local properties as a function of time at each position in the sample.

The evolutions can then be recorded and displayed, as shown in FIGS. 5 and 6.

Thanks to the device 10 according to the invention, it is possible to visualize at least a local property of the fluid in a bi-dimensional projection of the sample 12, covering at least a surface of the sample 12 at the same measurement time.

The acquisition time is very fast, less than 10 s, which allows the monitoring of evolutions of the local properties, in particular fluid proportions at each position in the bi-dimensional projection of the sample 12.

Contrary to devices available in the state of the art, the measurement is made globally, without relative movement or mechanical scanning of the X-ray source 22 relative to the sample 12.

The high stability of the X-ray source 22, the illumination of a reference sample 18 simultaneously with the measurement sample 12 and the simultaneous collection of data arising from various positions of the sample 12 by an array detector 24 allow the device 10 according to the invention to simply and efficiently acquire very relevant data.

The wide beam 62 generated by the X-ray source 22 is extremely stable and allows a detection whose resolution is defined by the size of the sensitive areas 80 of the detector 22. This allows a global monitoring of the sample 12, with a sample 12 of substantial size, as opposed to devices of the prior art in which a punctual determination is carried out at a plurality of successive points of the sample 12.

In a variation, shown in FIG. 3, at least one plug 34 comprises a cavity 120 intended to receive exclusively fluid coming from the sample or intended to be injected in the sample.

An image obtained from the cavity 120, representative of the absorbance of the liquid, is collected selectively on at least a sensing area 80. This signal can be used to characterize the different phases of the sample and improves the sensitivity of the calculation of the proportions.

In addition, the measurement of the fluid in the cavity 120 alleviates the need of further experiments, since it allows the recalculation of a reference image which corresponds to a state fully saturated in liquid phase.

The invention claimed is:

1. A device for analyzing a fluid in a sample of porous medium, comprising:
   a measurement cell, configured for receiving a sample of porous medium containing a fluid comprising one or more phases;
   an X-ray source, configured for illuminating the measurement cell with X-rays; and
   a detector, placed opposite the X-ray source with regards to the measurement cell, the detector being configured for receiving X-rays arising from the sample contained in the measurement cell;
   the detector comprising a plurality of sensing areas, at least a portion of which are arranged in a two-dimensional array, the plurality of sensing areas being configured for selectively detecting X-rays arising from at least one of different points on the surface of the sample or different points outside of the sample,
   the X-ray source being configured for illuminating the whole sample contained in the measurement cell without relative movement between the X-ray source and the sample,
   the device further comprising an analyzer configured for determining a local property of the fluid at a plurality of positions of the sample, based on signals detected simultaneously by sensing areas, at several measurement times, and without relative movement between the X-ray source and the sample.

2. The device according to claim 1, comprising a reference sample, positioned to be illuminated simultaneously with the measurement cell by the X-ray source, without relative movement between the X-ray source and the sample of porous medium, the detector having at least one sensing area of the plurality of sensing areas or another sensing area being configured for detecting X-rays arising from the reference sample.

3. The device according to claim 1, wherein the X-ray source comprises a hyperstable X-ray generator, the variation of the average number of photons per second produced by the generator being equal to a nominal value plus or minus 0.5% along time.

4. The device according to claim 1, wherein the X-ray source is intended to be permanently activated, the device comprising a shutter, positioned between the X-ray source and the measurement cell, the shutter being mobile between a position preventing the illumination of the measurement cell by the X-ray source and a position illuminating the measurement cell.

5. The device according to claim 1, comprising a controller for controlling temperature and pressure in the measurement cell.

6. The device according to claim 1, comprising at least a shield placed laterally around the measurement cell.

7. The device according to claim 1, wherein the measurement cell comprises a hollow container, receiving the sample of porous medium containing fluid, and at least one plug closing the hollow container.

8. The device according to claim 7, wherein the at least one plug comprises an internal open volume intended to receive fluid arising from the sample or directed towards the sample, the X-ray source being configured for illuminating the open volume, the detector comprising at least one selective sensing area of the plurality of sensing areas or another selective sensing area being configured for receiving X-ray arising from the open volume.

9. The device according to claim 1, wherein the analyzer is configured to determine at several measurement times local property of the fluid at various positions of the plurality of positions of the sample, wherein the sample is in a static state throughout the several measurement times at each of the various positions.

10. Method of analyzing a fluid comprising one or more phases in a sample of porous medium, comprising:
   providing a device, comprising:
      a measurement cell, configured for receiving a sample of porous medium containing a fluid comprising one or more phases;
      an X-ray source, configured for illuminating the measurement cell with X-rays; and
      a detector, placed opposite the X-ray source with regards to the measurement cell, the detector being configured for receiving X-rays arising from the sample contained in the measurement cell;
      the detector comprising a plurality of sensing areas, at least a portion of which are arranged in a two-dimensional array, the plurality of sensing areas being configured for selectively detecting X-rays arising from at least one of different points on the surface of the sample or different points outside of the sample,
      the X-ray source being configured for illuminating the whole sample contained in the measurement cell without relative movement between the X-ray source and the sample, the device further comprising an analyzer configured for determining a local property of the fluid at a plurality of positions of the sample, based on signals detected simultaneously by the sensing areas, at several measurement times, and without relative movement between the X-ray source and the sample, the measurement cell containing a sample of porous medium containing fluid;

the method further comprising repeating the following steps:

illuminating at least a surface of the sample with the X-ray source, without relative movement between the X-ray source and the sample;

selectively detecting X-rays arising from different points of the surface by the plurality of sensing areas of the detector; and determining a local property of the fluid at a plurality of positions of the sample, based on signals detected simultaneously by the sensing areas.

11. Method according to claim 10, wherein the illumination comprises passing X-rays arising from the X-ray source through a reference sample simultaneously with illuminating the measurement cell and selectively detecting X-rays arising from the reference sample with a selective sensing area of the plurality of sensing areas or another selective sensing area of the detector.

12. Method according to claim 10, comprising controlling the pressure of the sample in the measurement cell, and controlling the temperature of the sample in the measurement cell, during the illumination step.

13. The method according to claim 12, comprising controlling the pressure of the sample in the measurement cell above the atmospheric pressure.

14. Method according to claim 10, wherein the determination comprises calculating a fluid content in one or more phases at least at a plurality of positions on the surface of the sample, based on the signal detected by each sensing area.

15. The method according to claim 10 comprising repeating each of illuminating at least a surface of the sample with the X-ray source, selectively detecting X-rays arising from different points of the surface by a plurality of sensing areas of the detector and determining a local property of the fluid at a plurality of positions of the sample, based on signals detected simultaneously by the sensing areas, at several measurement times, without relative movement between the X-ray source and the sample, at a frequency below 1 Hz.

16. The method according to claim 10, wherein the sample contained in the measurement cell is in a static state throughout a plurality of repeating sequences of the illuminating, selectively detecting, and determining at each of various positions of the plurality of positions of the sample.

* * * * *